United States Patent
Bruce et al.

(10) Patent No.: US 7,179,963 B2
(45) Date of Patent: Feb. 20, 2007

(54) MAIZE CLAVATA3-LIKE POLYNUCLEOTIDE SEQUENCES AND METHODS OF USE

(75) Inventors: Wesley B. Bruce, Grimes, IA (US); Lisa J. Newman, Urbandale, IA (US); Hajime Sakai, Newark, DE (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 506 days.

(21) Appl. No.: 10/430,523

(22) Filed: May 6, 2003

(65) Prior Publication Data
US 2003/0226178 A1    Dec. 4, 2003

Related U.S. Application Data

(60) Provisional application No. 60/380,170, filed on May 6, 2002, provisional application No. 60/392,918, filed on Jul. 1, 2002.

(51) Int. Cl.
*A01H 1/00* (2006.01)
*C07H 21/04* (2006.01)
*C07K 14/415* (2006.01)
*C12N 15/29* (2006.01)

(52) U.S. Cl. ............... 800/295; 435/6; 435/69.1; 435/71.1; 435/183; 435/410; 435/419; 435/320.1; 530/350; 530/370; 536/23.1; 536/23.2; 536/23.6; 800/278

(58) Field of Classification Search ............... 435/6, 435/69.1, 468, 419, 252.3, 320.1, 183; 530/370; 536/23.6; 800/278, 295
See application file for complete search history.

(56) References Cited

U.S. PATENT DOCUMENTS 5,880,328 A * 3/1999 Ryals et al. ................. 800/298

* cited by examiner

*Primary Examiner*—Phuong T. Bui
(74) *Attorney, Agent, or Firm*—Pioneer Hi-Bred International

(57) ABSTRACT

Methods and compositions for modulating development and/or developmental pathways are provided. The compositions of the present invention comprise nucleic acid and amino acid sequences. Particularly, the nucleotide sequence (SEQ ID NO:1, 3, 4 or 7) and amino acid sequence (SEQ ID NO:2 or 8) for a maize CLAVATA3-like (CLV3-like) polypeptide are provided. Methods are provided for the expression of the CLV3-like sequences in a host plant or plant cell to modulate plant development and/or developmental pathways. The methods of the invention find use in controlling or modulating cell division, differentiation and development. In particular, the sequences of the present invention find use in modulating meristem development. Transformed plants, plant cells, tissues, and seed are also provided.

14 Claims, 8 Drawing Sheets

FIGURE 1

```
Query:  57  GAEEDLSTTGFGAESE-REVPTGPDPIHHHARGPRR  91
            G  E    T G G   E R  VP+GPDP+HHH   PR+
Sbjct:  53  GEAEKAKTKGLGLHEELRTVPSGPDPLHHHVNPPRQ  88
```

Figure 3A

GCAGAGGGTTTTGGAGCAGGCAAGCCTGGCTCTTCTTCTTGTTCCTCCATCTCTTCCGTCGCCTTGCCGCTGTTGGCGCTGCCGTACGCCGAG
GCCGCCGCGTCTGCCGTCGCCGCATGGCTCACGCGGCTCACGCGGCCCGTCGCTCGCCGTCGCCTGCTCCGTCGCCTGTGATCTTGGCCTGCCGCCCGCCGC
CTCGTCCTACCGGGAGCGGCTGCATTGCGACGGCTGCGAGACAGCGGAGCCCATGGACACCGCGCAGGGCTTGCGGGAGAAGGCGGACG
TGAACAAGGGCGCGGAGGAGGACCTGAGCACCACAGGGTTCGGCGCCGAGTCGGAGAGGGAGTGCCGAGCGGAGACCCCATCCAC
CACCACGCCCGGGGCCCAAGGCGGCAGTCGCCTTGATCGTCATGCGGATGATCCTGCTCTTTCTTGTTCTTTAAATGTATCTGCCATGCACCTTTGGTTC
TGGTCTTTGATCAGGCGGGCGTGAACCGGATTCCACGATGATCCTGCTCTTGTTCTTTAAATGTATCTGCCATGCACCTTTGGTTC
TAATTCCATTGTTGTAGTAGGAAGCAGCATCCACCTATCAACTATCATCAAAACCCCTATGTTTTGGCGTGCCAATTAGAGAAAGG
GAATTACAGCGCGATTCATATATAAGTGTACAATGAATTCCACGTATGAGTTGTTCTTTCCCTCGTAATTTTGTCATCTTGTTTTG
TTGCTGGTTCAAAAAAAAAAAAAAAA

Figure 3B mahaavvallavavilaclpppaassyrgaaalrrletaepmdtagglrekadvnkgaeedlsttgfgaese<u>rerevptgpdpihh</u>hargp
rrqsp

Figure 4A

ACCAGACGGGCGAAACCAACTCTCTGCGGCAGAGGGCGACGGCAGAGGGTCTTGGAGCAGGCAAGCCTGGCTCTTCTTGTTCCTCCAT
CTCTTCCGTCGCCTTGCCGCTGTTGGCGCTTGGCCTCTGCCGCCGCTCTGCCGTCTGCCGGGGAGCTCACGCGCCGTCGTCGCCTTGCT
CGCCGTCGCTGTGATCTTGGCCTGCTTGCCGCTCCTCGTCCTACCGGGAG*gtacgtaaaacgcgcccgcgcatcgc*
*aaccaaacgtgttttcttggttcttccggcgcacccaaaacctgacgttttcgcccgcggcacagCGGCTGCATTGCGACGGCTCG*
AGACACGGGAGCCCATGGACACCGCGACAGGGCTTGCGGAGAAGGCGACGTGAACAAGgt*aaaaatacaaagacgcccgccgtgc*
*tgcgggctagggtcaaggaaaggcggctctttttctgctggtctcttttcgattctccggctcgatcttccggcgtgcaggGGCGGAG*
GAGGACCTGAGCACGACAGGGTTCGGCGCCGAGTCGGAGAGGAGGTGCCGACGGAGTCCTCGCTTCCTGGAAGTTTGTGTCTTGATCAGGCGG
AAGGCGCAGTCGCCTGATCGTCATGCGCGGTGGATCCTCGCTTCCGATGCCATGCACCTTTGTTCTTAATTCCATTGTTGTAG
GCGTGAACCGGATTCCACGATGATCCTGAAGGGCGAATTCTCTTAAATGTATCTCGCACCTTTGTTCTTAATTCCATTGTTGTAG
TAGGGAAGCAGCATCCACCTATCAA

Figure 4B

ATGGCTCACGCGGCCGTCGTCGCCTTGCTCGCCGTCGTGATCTTGGCCTGCTTGCCGCCGCCTCGTCCTACCGGGGAGC
GGCTGCATTGCGACGGCTCGAGACAGGCTCGAGACACAGCCGAGCCCATGACCGCGCAGGGCTTGCGGGAGAAGGCGGACGTGAACAAGGGCGGAGG
AGGACCTGAGCACGACAGGGTTCGGCGCCGAGTCGGAGAGGAGGTGCCGACGGAGTCCTCGACCCCATCCACCACCGCGCCCCGGGGCCA
AGGCGGCAGTCGCCTTGA

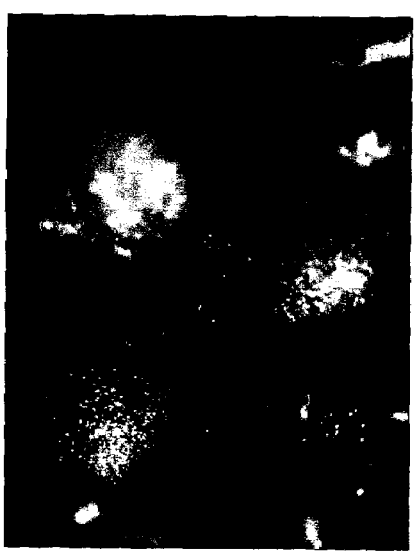
Figure 5

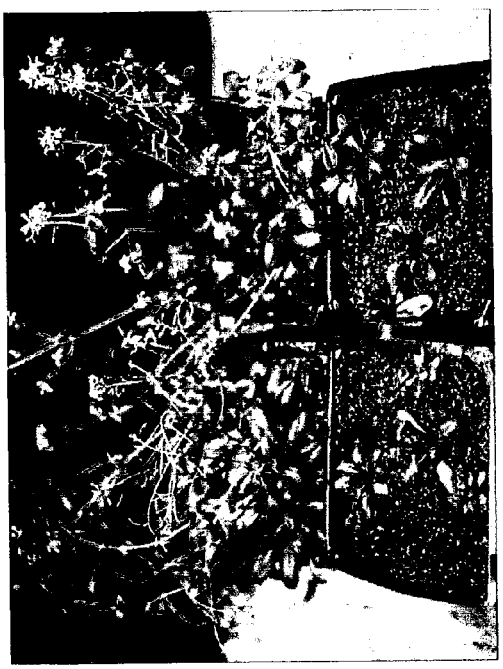
Figure 6

```
                  1                                                50
Os_CLV3-like   (1) ---------------MSPPAAAAAAASSSQPAAAALQRAETTATMYTAKELRE
ZmCLV3-like    (1) MAHAAVVALLAVAVILACLPPPAASSYRGAAALRRLETAEPMDTAQGLRE
AtCLV3         (1) ---MDSKSFVLLLLFCFLFLHDASDLTQAHAHVQGLSNRKMMMKMESE
                  51                                               100
Os_CLV3-like  (40) KQDVTKGAEEDVTTTTTTGFGAESE-REVPTGPDPIHHHGRGPRRQS--
ZmCLV3-like   (51) KADVNKGAEEDLS----TTGFGAESE-REVPTGPDPIHHHARGPRRQSP-
AtCLV3        (48) -WVGANGEAEKAK----TKGLGLHEELRTVPSGPDPLHHHVNPPRQPRNN
                  101
Os_CLV3-like  (87) ----
ZmCLV3-like   (95) ----
AtCLV3        (93) FQLP
```

FIGURE 8

MAIZE CLAVATA3-LIKE POLYNUCLEOTIDE SEQUENCES AND METHODS OF USE

CROSS-REFERENCE TO RELATED APPLICATION

This utility application claims the benefit U.S. Provisional Application No. 60/380,170, filed May 6, 2002, and U.S. Provisional Application No. 60/392,918, filed, Jul. 1, 2002, all of which are incorporated herein by reference.

FIELD OF THE INVENTION

The invention relates to the field of the genetic manipulation of plants, particularly the modulation of gene activity and development in plants.

BACKGROUND OF THE INVENTION

Leaves and the axillary meristems that generate branches and flowers are initiated in regular patterns from the shoot apical meristem. The cells of the shoot apical meristem summit serve as stem cells that divide to continuously displace daughter cells to the surrounding regions, where they are incorporated into differentiated leaf or flower primordia. The meristems are thus capable of regulating their size during development by balancing cell proliferation with the incorporation of cells into new primordia.

Several mutations have been identified in *Arabidopsis* that cause meristem enlargement including, for example, the clavata (clv) mutations, mgoun1 and mgoun2, fasciata1 and fasciata2 and the fully fasciated mutation. CLAVATAL1 (CLV1) is a member of a plant-specific family of receptor protein kinases that span the membrane and allow cells to recognize and respond to their extracellular environment. CLV2 is a membrane bound leucine-rich-repeat (LRR) protein that binds with CLV1. CLV3 appears to be a ligand, or a molecule involved in ligand synthesis or binding that is produced in the shoot apical meristem region. Loss of CLV1, CLV2, or CLV3 activity in *Arabidopsis* causes accumulation of undifferentiated cells in the shoot apex, indicating that CLV genes together promote the timely transition of stem cells into differentiation pathways, or repress stem cell division, or both.

Loss of CLV1 or CLV3 activity in *Arabidopsis* presents as an enlargement of the shoot apical meristem and the generation of extra floral organs (Fletcher et al. (1999) *Science* 283:1911–1914; Taguchi-Shiobare et al. (2001) *Genes and Development* 15:2755–5766; and, Trotochaud et al. (1999) *The Plant Cell* 11:393–405). The shoot apical meristems of clv mutant plants enlarge progressively throughout development, such that by the time the plant makes the transition to flowering the meristem has often undergone fasciation and groups as a mound instead of a point. The production of such fasciated shoot apical meristems by a clv mutant plant indicates that the wild-type function of CLV1, CLV2, and CLV3 is to restrict shoot apical meristem activity. Mutants with fasciated shoot apical meristems resembling those of the clv mutants have also been reported in tomato (Merton et al. (1954) *Am. J. Bot.* 41:726–32 and Szymkowiak et al. (1992) *Plant Cell* 4:1089–100), soybean (Yamamoto et al. (2000) *Biochim. Biophys. Acta.* 1491:333–40), and maize (Taguchi-Shiubara et al. (2001) *Genes Dev.* 15:2755–66).

In maize, a fasciated ear2 (fea2) mutant has been identified (Taguchi-Shiubara et al. (2001) *Genes Dev.* 15:2755–66). fea2 encodes an LRR protein that is targeted to the plasma membrane, suggesting that it acts as a receptor, and is most closely related to the CLV2 gene of *Arabidopsis*. fea2 plants develop larger meristems during inflorescence and floral shoot development. In addition, ear inflorescence meristems show severe fasciation, suggesting that fea2 normally acts to limit the growth of these meristems. In addition, fea2 plants have an increase in floral organ number. Male flowers have an increase in stamen number and female flowers have an increase in carpel number. fea2 plants also have longer pedicels in the tassel spikelets, a phenotype that is similar of the longer flower pedicel phenotype of clv2 mutants. These results suggest that the CLAVATA pathway is functionally conserved in monocot species.

It is desirable to be able to control the size and appearance of shoot and floral meristems, to give increased yields of leaves, flowers, and fruit. Accordingly, it is an object of the invention to provide novel methods and compositions for the modulation of meristem development.

BRIEF SUMMARY OF THE INVENTION

The present invention provides maize CLAVATA3-like (CLV3-like) nucleotide and amino acid sequences. The sequences of the invention find use in modulating development and developmental pathways, particularly, modulating meristem development.

The present invention provides an isolated polypeptide selected from the group consisting of (a) a polypeptide comprising an amino acid sequence set forth in SEQ ID NO:2 or 8; (b) a polypeptide encoded by a nucleotide sequence comprising the sequence set forth in SEQ ID NO:1, 3, 4 or 7; (c) a polypeptide encoded by a nucleotide sequence that hybridizes under stringent conditions to the complement of a nucleotide sequence comprising the sequences set forth in SEQ ID NOS: 1, 3, 4 or 7, wherein said stringent conditions comprise hybridization in 50% formamide, 1M NaCl, 1% SDS at 37° C., and a wash in 0.1×SSC at 60° C. to 65° C.; (d) a polypeptide comprising an amino acid sequence having at least 70% sequence identity to the sequence set forth in SEQ ID NO:2 or 8, wherein said sequence modulates meristem development; and, (e) a polypeptide comprising at least 15 contiguous amino acids of SEQ ID NO:2 or 8.

The present invention further provides an isolated nucleic acid molecule selected from the group consisting of (a) a nucleic acid molecule comprising a nucleotide sequence set forth in SEQ ID NO:1, 3, 4 or 7; (b) a nucleic acid molecule comprising a nucleotide sequence encoding an amino acid sequence set forth in SEQ ID NO:2 or 8; (c) a nucleic acid molecule comprising at least 15 consecutive nucleotides of the complement of SEQ ID NO:1, 3, 4, or 7; (d) a nucleic acid molecule comprising at least 15 consecutive nucleotides of SEQ ID NO:1, 3, 4 or 7; (e) a nucleic acid molecule comprising a nucleotide sequence that hybridizes under stringent conditions to the complement of nucleotide sequence set forth in SEQ ID NO:1, 3, 4, or 7, wherein said stringent conditions comprise hybridization in 50% formamide, 1M NaCl, 1% SDS at 37° C., and wash in 0.1×SSC at 60° C. to 65° C.; and, (f) a nucleic acid molecule comprising a nucleotide sequence having at least 70% sequence identity to the sequence set forth in SEQ ID NO:1, 3, 4, or 7, wherein said sequence encodes a polypeptide that modulates meristem development.

Compositions of the invention further include host cells, plants, plant cells and seeds having stably incorporated into their genome at least one nucleotide construct comprising a nucleotide sequence of the invention. Methods for making such cells, plants, and seeds are further provided. It is recognized that a variety of promoters will be useful in the invention, the choice of which will depend in part upon the desired level of expression of the disclosed nucleotide sequences. It is recognized that the levels of expression can be controlled to modulate the levels of expression in the plant cell.

In particular, the methods and compositions can be used to modulate plant development. More specifically, methods and compositions of the invention may be used for modulating meristem development. The method involves stably transforming a plant with a CLV3-like nucleotide sequence and expressing said sequence in a plant or plant cell. Methods are also provided for modulating the level of a polypeptide in a plant or plant cell comprising introducing into the plant or plant cell a nucleic acid molecule of the invention encoding said polypeptide and expressing the nucleic acid molecule for a time sufficient to modulate the level of said polypeptide. In one embodiment, the nucleotide sequence of the invention is operably linked to a drought-inducible promoter.

In other methods of the invention, the level of a polypeptide in a plant or plant cell is modulated by providing a plant comprising an mRNA having the sequence set forth in SEQ ID NO:1, 3, 4 or 7, and introducing into the plant or plant cell a nucleotide sequence comprising at least 15 consecutive nucleotides of the complement of SEQ ID NO:1, 3, 4 or 7, wherein the nucleotide sequence inhibits expression of the mRNA in the plant or plant cell.

BRIEF DESCRIPTION OF THE DRAWINGS

FIG. 1 provides an amino acid sequence alignment of the CLAVATA3-like sequence from maize with the CLAVATA3 amino acid sequence from *Arabidopsis*. The top sequence in the alignment corresponds to amino acid 57 to 91 of SEQ ID NO:2, while the bottom sequence corresponds to amino acids 53 to 88 of GenBank Accession No. Q98ZF04 (SEQ ID NO:5).

FIG. 3A provides the nucleic acid sequence of the cDNA CLAVATA3-like sequence of the invention (SEQ ID NO:1) and FIG. 3B provides the corresponding amino acid sequence (SEQ ID NO:2). The conserved 14 amino acid region commonly found in CLAVATA3 homologs (Cock et al. (2001) *Plant Physiology* 126:939–942) corresponds to amino acids 73 to 87 of SEQ ID NO:2 and is underlined in FIG. 3B.

FIG. 4A provides the nucleic acid sequence of a genomic fragment containing the CLAVATA3 gene. The genomic fragment contains two introns (similarly placed to the *Arabidopsis* CLV3 gene) that are indicated by lower case italics and underlined. The coding sequence of the genomic fragment with the introns removed is provided in FIG. 4B and corresponds to the nucleotide sequence of SEQ ID NO:3.

FIGS. 5(*a, b, c*, and *d*) illustrates constitutive expression of zmCLV3 in young plantlets of *Arabidopsis* sp. This causes an arrest of SAM development in wild type and clv3 mutant backgrounds limiting the number of growing leaves to a few. FIG. 5*a* shows 35S::zmCLV3 in clv3-1, 5*b* shows another transgenic line of 35S::zmCLV3 in clv3-1, 5*c* shows 35S::zmCLV3 in wild type tissue, and 5*d* shows 35S::Esr1 in clv3-1 where several young growing leaves can be observed similar to wild type alone.

FIGS. 6(*a, b* and *c*) shows *Arabidopsis* plants with constitutive expression of zmCLV3 having similar phenotype to wuschel which is essentially an equivalent phenotype of constitutive expression of the atCLV3 (Brand et al. (2000) *Science* 289:617–619). FIG. 6*a* is a photograph of wild type (two trays on left) and clv3-1 (two trays on right) plants growing with (two front trays) and without (two back trays) transformation with zmCLV3. FIG. 6*b* is a close up of 35S::zmCLV3 in wild type tissue, and FIG. 6*c* is a close up of 35S::zmCLV3 in clv3-1 tissue.

FIG. 8 is the CLUSTALW-derived protein sequence alignment of rice (SEQ ID NO: 8) and maize (SEQ ID NO: 2) CLV3-like with the *Arabidopsis* CLV3 protein sequence (GenBank Accession No. Q98ZF04) using default settings. Red-boxed shows identical amino acids, blue shows those aa identical between two of the three sequences, green and grey-boxed shows conservative substituted amino acid matches.

DETAILED DESCRIPTION OF THE INVENTION

Overview

Figure 2:
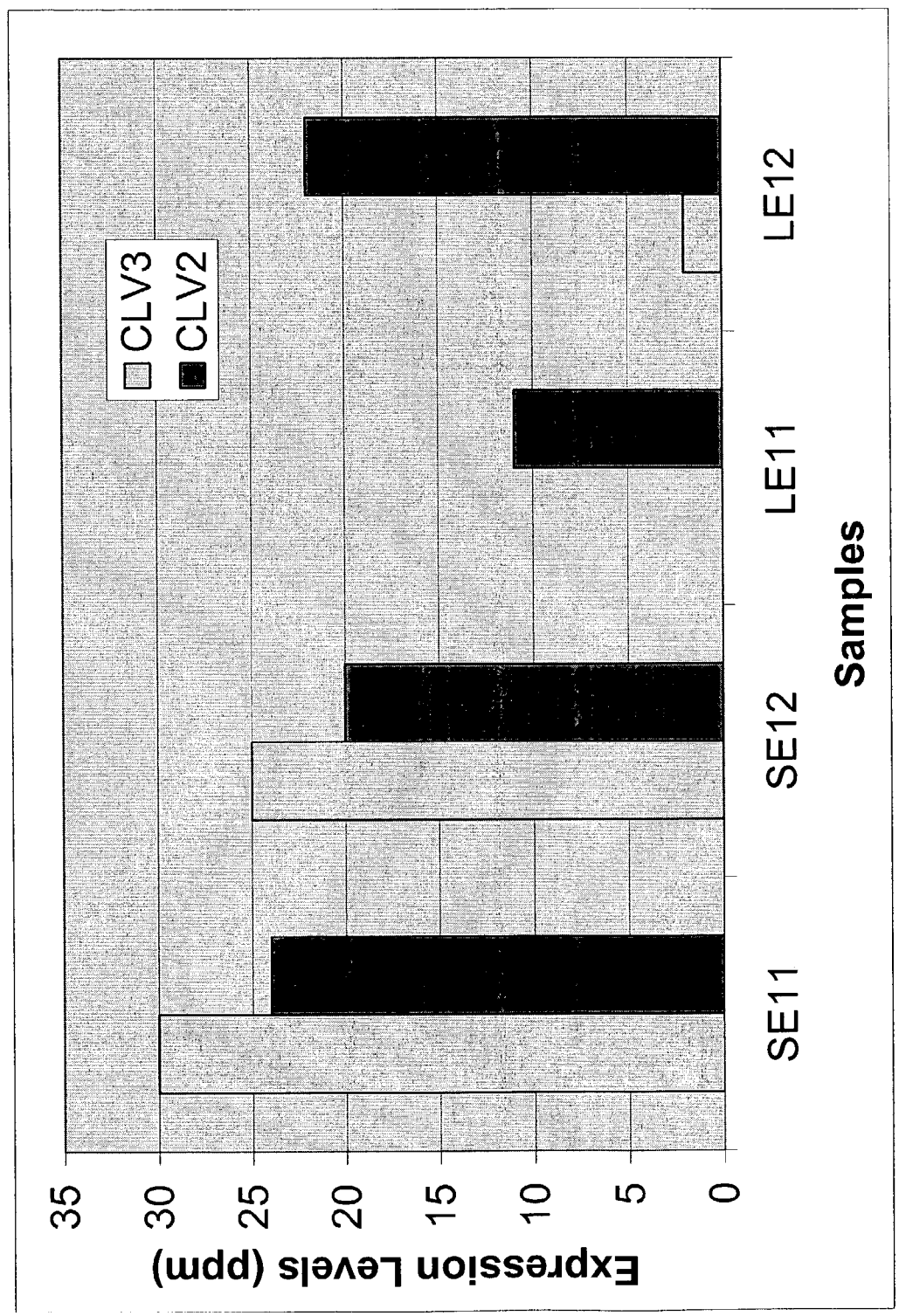
FIG. 2 provides expression levels of maize orthologs of CLV3 and CLV2 in whole immature ears from long ear (LE) and short ear (SE) inbred lines at two vegetative stages, V11 and V12.

The compositions of the present invention comprise nucleic acid and amino acid sequences. Particularly, the nucleotide sequence (SEQ ID NO:1, 3, or 4) and amino acid sequence (SEQ ID NO:2) for a maize CLAVATA3-like (CLV3-like) polypeptide are provided.

The CLV3-like polypeptide of the present invention is approximately the same length as CLAVATA3 from *Arabidopsis* (Fletcher et al. (1999) *Science* 283:1911–1914), and, as shown in FIG. 1, the sequences of the present invention share homology with the *Arabidopsis* CLAVATA3 amino acid sequence. The top sequence in the alignment of FIG. 1 corresponds to amino acid 57 to 91 of the maize CLV3-like polypeptide (SEQ ID NO:2), while the bottom sequence corresponds to amino acids 53 to 88 of GenBank Accession No. Q98ZF04 (SEQ ID NO:5). The CLV3-like polypeptide of the present invention further contains a conserved region of 14 amino acid that is present in *Arabidopsis* CLV3. This conserved region corresponds to amino acids 72 to 85 of SEQ ID NO:2. The present invention is the only other functional ortholog of *Arabidopsis* CLV3 known to date.

A signal sequence prediction program, SignalP v 1.1 predicts the presence and location of signal peptide cleavage sites in amino acid sequences from different organisms: Gram-positive prokaryotes, Gram-negative prokaryotes, and eukaryotes. The method incorporates a prediction of cleavage sites and a signal peptide/non-signal peptide prediction based on a combination of several artificial neural networks (Nielsen, et al. (1997) *Int. J. Neural Sys.* 8:581–599). Using SignalP v 1.1 for the maize CLV3-like and *Arabidopsis* CLV3 protein sequences, it showed that both have a highly predictive signal sequence in approximately the first 20 amino acids. The signal sequence is important in directing the polypeptide to the cell surface following its cleavage. It is known that the *Arabidopsis* CLV3 is transported to the extracellular space (Rojo, et al. (2002) *Plant Cell*, 14:969–77).

When compared to the CLV3-like cDNA sequence (SEQ ID NO:1), the genomic sequence (SEQ ID NO:4) of the CLV3-like transcribed region shows the presence of two introns (SEQ ID NO: 4 at 238–335, and 415–525), the same as that of the *Arabidopsis* CLV3 gene. Genomic sequences from four maize inbred lines show that the CLV3-like coding sequences are identical but some sequence polymorphisms exist in the introns, 5' UTR and 3' UTR. For two maize inbred lines A and B, the ears have low floret number per kernel row while the two remaining lines, C and D, have significantly higher floret number per kernel row. Comparing the genomic sequences of A and B show that they are 99.8% homologous (2 out of 826 nucleotide differences) whereas the CLV3-like genomic sequences of either A or B compared to C and D show 97.3 and 96.8% homology (22/826 and 27/826 nucleotide differences), respectively. This suggests that the two inbred lines with lower floret numbers per row and short ears have a very similar allele of CLV3-like gene. The short ear alleles are significantly different from the CLV3-like alleles of C and D inbreds both having higher floret number per row and a tendency toward longer ears.

The CLV3-like sequence of the present invention was isolated from a maize library (5 days after silking ovules) that included meristematic tissues. As discussed in further detail below, the expression of the CLV3-like sequence of the present invention was shown to be more active in a short ear elite maize line than in a long ear line. A homolog of CLV3 would be predicted to be more active in the immature ear tissue of a short ear line than in a long ear line, since this sequence would negatively regulate meristem maintenance genes, such as, for example, a maize homolog WUSCHEL or POLTERGEIST. For a review see, for example, Fletcher et al. (2002) *Annu. Rev. Plant Biol.* 53:45–66.

Additionally, in situ RNA hybridization (Jackson et al. (1991) In: *Molecular Plant Pathology: A Practical Guide* (D J Bowles, S J Gurr, & M McPhereson, eds), Oxford University Press) of the CLV3-like gene in developing ears of maize clearly revealed evidence of CLV3-like mRNA in the meristems of the incipient ear florets as predicted by similarity in function to *Arabidopsis* CLV3. Two insertional mutant maize lines by the transposable element Mutator were identified in the CLV3-like gene by the method essentially as described (Bensen, et al. (1995) *Plant Cell* 7:75–84) producing mildly fasciated ears similar to what was observed by fea2mutant lines (Taguchi-Shiubara et al. (2001) *Genes Dev.* 15:2755–66). Consequently, these data support that the maize CLV3-like of the present invention is a CLV3 functional homolog.

Methods are therefore provided for the expression of the CLV3-like sequences in host cells, host plants, or plant cells to modulate plant development and/or developmental pathways. Thus, the invention finds use in controlling or modulating cell division, differentiation, and development. In particular, the sequences of the present invention find use in modulating meristem development.

As discussed in further detail below, by "modulating meristem development" is intended any alteration in the meristem phenotype including, for example, an alteration in the formation and maintenance of the meristem and/or an alteration of size and appearance of shoot and floral meristems. Such modulations in meristem development may result in an increase or a decrease in meristem size and/or an increase or decrease in the yield of leaves, flowers, and/or fruit.

Compositions

Compositions of the invention include nucleic acid and amino acid sequences that are involved in modulating plant development and developmental pathways. In particular, the present invention provides for isolated nucleic acid molecules comprising nucleotide sequences encoding the amino acid sequences shown in SEQ ID NO:2. Further provided are polypeptides having an amino acid sequence encoded by a nucleic acid molecule described herein, for example those set forth in SEQ ID NOS: 1, 3, or 4, and fragments and variants thereof.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence bind receptors, influence signal transduction, and/or retain the ability to modulate meristem development (i.e., prevent meristem enlargement). Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, about 150, about 200, about 250, about 300, about 350, about 400, about 450, about 500 and up to the full-length nucleotide sequence encoding the proteins of the invention. Alternatively, the fragment can comprises nucleotides 1–50, 50–100, 100–150, 150–200, 200–250, 250–300, 300–350, 350–400, 400–450, and 450–500. Other fragments of the polypeptide of SEQ ID NO:2 include amino acids 1–20, amino acids 21–40, amino acids 41–60, amino acids 61–80, and amino acids 81–94.

A fragment of a CLV3-like nucleotide sequence that encodes a biologically active portion of a CLV3-like protein of the invention will encode at least 15, 25, 30, 50, 60, 70, 80, 90, or 96 contiguous amino acids, or up to the total number of amino acids present in a full-length CLV3-like protein of the invention (for example, 96 amino acids for SEQ ID NO:2). Fragments of a CLV3-like nucleotide sequence that are useful as hybridization probes or PCR primers generally need not encode a biologically active portion of a CLV3-like protein.

Thus, a fragment of a CLV3-like nucleotide sequence may encode a biologically active portion of a CLV3-like protein, or it may be a fragment that can be used as a hybridization probe or PCR primer using methods disclosed below. A biologically active portion of a CLV3-like protein can be prepared by isolating a portion of one of the CLV3-like nucleotide sequences of the invention, expressing the encoded portion of the CLV3-like protein (e.g., by recombinant expression in vitro), and assessing the activity of the encoded portion of the CLV3-like protein. Nucleic acid molecules that are fragments of a CLV3-like nucleotide sequence comprise at least 16, 20, 50, 75, 100, 150, 200, 250, 300, 350, 400, 450, 500 nucleotides, or up to the number of nucleotides present in a full-length CLV3-like nucleotide sequence disclosed herein (for example, 740 nucleotides, 282 nucleotides, or 826 nucleotides for SEQ ID NOS: 1, 3, or 4, respectively).

By "variants" is intended substantially similar sequences. For nucleotide sequences, conservative variants include those sequences that, because of the degeneracy of the genetic code, encode the amino acid sequence of one of the CLV3-like polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a CLV3-like protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, bind receptors, influence signal transduction, and/or retain the ability to modulate meristem development (i.e., prevent meristem enlargement), as described herein. Such variants may result from, for example, genetic polymorphism or from human manipulation. Biologically active variants of a native CLV3-like protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the CLV3-like proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired activity (i.e., bind receptors, influence signal transduction, and/or retain the ability to modulate meristem development (i.e., prevent meristem enlargement)). Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. Plants exhibiting modulated meristem development can be selected using visual observation. See, for example, U.S. Pat. Nos. 5,637,785; 6,002,069; 5,859,338; 6,025,483, and Fletcher et al. (1999) *Science* 283:1911–1914, all of which are herein incorporated by reference. Alternatively, assays to measure receptor binding are also routine. See, for example, Trotochaud et al. (2000) *Science* 289:613–617, which is herein incorporated by reference.

Variant nucleotide sequences and proteins also encompass sequences and proteins derived from a mutagenic and recombinogenic procedure such as DNA shuffling. With such a procedure, one or more different CLV3-like coding sequences can be manipulated to create a new CLV3-like sequence possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the CLV3-like gene of the invention and other known sequences involved in meristem maintenance or development (such as other CLV3 homologs) to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997)

*Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391: 288–291; and U.S. Pat. Nos. 5,605,793 and 5,837,458.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG® programs (Accelrys, Inc., San Diego, Calif.) .). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al., (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire CLV3-like sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode for a CLV3-like protein and which hybridize under stringent conditions to the CLV3-like sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the CLV3-like sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire CLV3-like sequence disclosed herein, or one or more portions thereof, may be used as a probe capable of specifically hybridizing to corresponding CLV3 sequences and messenger RNAs. To achieve specific hybridization under a variety of conditions, such probes include sequences that are unique among CLV3-like sequences and are preferably at least about 10 nucleotides in length, and most preferably at least about 15, about 20 or about 50 nucleotides in length. Such probes may be used to amplify corresponding CLV3-like sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M_NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.$+16.6$ (log M)$+0.41$ (% GC)$-0.61$ (% form)$-$ 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

As discussed above, the CLV3-like sequences of the present invention are predicted to limit the growth of meristem structures by regulating cell division in the meristem. However, fragments and variants of the CLV3-like sequences that encode CLV3-like polypeptides of the invention are not limited to retaining the native biological activity of the protein. It is recognized that the sequences of the invention encoding the CLV3-like polypeptides may be modified such that expression of the polypeptide results in meristem enlargement. Consequently, sequences encoding dominant-negative CLV3-like polypeptide are encompassed by the present invention. In this embodiment, the variants and fragment of the CLV3-like polypeptide interfere with the function of the normal, endogenous CLV3-like protein. Thus, the action of the endogenous CLV3-like polypeptide can be blocked without inactivating the structural CLV3-like gene sequence or its RNA.

A fragment of a CLV3-like nucleotide sequence that encodes a CLV3-like protein having dominate negative activity will encode at least 15, 25, 30, 50, 60, 70, 80, 90, or 94 contiguous amino acids, or up to the total number of amino acids present in a full-length CLV3-like protein of the invention (for example, 94 amino acids for SEQ ID NO:2). Alternatively, a variant of a CLV3-like protein of the invention that has dominant negative activity will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. In addition, a variant of a CLV3-like polypeptide having dominate negative activity may differ from that protein by as few as 1–15 amino acid residues, as few as 1–10, such as 6–10, as few as 5, as few as 4, 3, 2, or even 1 amino acid residue.

Methods of obtaining dominant negative mutations are known in the art. See, for example, Attardi et al. (1993) *Proc. Natl. Acad. Sci* 90:10563, Lloyd et al. (1991) *Nature* 352:635; Logeat et al. (1991) *EMBO* 10:1827; Mantovani et al. (1995) *J. Biol. Chem* 269:20340, all of which are herein incorporated by reference. A CLV3-like sequence having dominant negative activity will decrease the activity of the endogenous CLV3-like polypeptide. Functional assays to identify CLV3-like sequences having dominant negative activity include, expression of the CLV3-like fragment or variant in a plant or plant cell and visually assaying for a modulation in meristem development, particularly an enlargement of the meristem. In shoot apical meristems this enlargement can lead to fasciation, where the meristem grows large, causing the stem to become straplike, and leaves and flowers to be produced in great profusion. In flowers, the enlargement leads to an increase in the number of floral organs, including an increase in carpel number, which increase fruit size and seed numbers. A more complete description of the phenotypes encompassed by the term meristem enlargement is found below.

Expressions of the Sequences

The nucleic acid sequences of the present invention can be expressed in a host cell such as bacteria, yeast, insect, mammalian, or preferably plant cells. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

As used herein, a host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The CLV3-like sequences of the invention are provided in expression cassettes or nucleotide constructs for expression in the plant of interest. The cassette will include 5' and 3' regulatory sequences operably linked to a CLV3-like sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the CLV3-like sequence to be under the transcriptional regulation of the regulatory regions. The expression cassette may additionally contain selectable marker genes.

The expression cassette will include in the 5'-3' direction of transcription, a transcriptional and translational initiation region, a CLV3-like sequence of the invention, and a transcriptional and translational termination region functional in plants. The transcriptional initiation region, the promoter, may be native (or analogous) or foreign (or heterologous) to the plant host. Additionally, the promoter may be the natural sequence or alternatively a synthetic sequence. By "foreign" or "heterologous" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of the CLV3-like RNA/protein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al., (1987) *Nucleic Acid Res.* 15:9627–9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); polyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334: 721–724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in plants. Such constitutive promoters include, for example, the core promoter of the Rsyn7 (PCT Application Serial No. US99/03863); Scp1 promoter (U.S. Pat. No. 6,072,050), rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

In specific embodiments it will be beneficial to express the gene from an inducible promoter. For example, chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

In another embodiment, the promoter is a drought-inducible promoter. By drought-inducible promoter is intended a promoter that is inducible under conditions of osmotic stress. For example, the RAB-17 promoter is induced by drought as well as other stresses, presumably as a result of its regulation by the plant hormone ABA. See for example, Vilardell et al. (1990) *Plant Mol. Biol.* 14:423–432. Alternatively, the promoter of the *Arabidopsis* Atmyb2 gene can be used as a general ABA-responsive, drought and stress-induced promoter (Urao et al. (1993) *Plant Cell* 5:1529–1539). Other drought-inducible promoters include 26-g from *Pisum sativum* (Guerrero et al. (1988) *Plant Physiol* 88:401–408; Guerrero et al. (1990) *Plant Mol Biol* 15: 11–26), trg-31 from tobacco (Guerrero et al. (1993) *Plant Mol Biol* 21:929–935) btg-26 from *Brassica napus* (U.S. Pat. No. 6,084,153); or the promoters from the rd29B, and the AREB1, 2, and 3 genes (Uno et al. (2000) *Proceedings of the National Academy of Sciences* 97:11632–11637; Yamaguchi-Shinozaki et al. (1993) *Mol. Gen. Genet* 236: 331–40; and, Yamaguchi-Shinozaki et al. (1994) *Plant Cell* 6:251–64, all of which are herein incorporated by reference).

Alternatively, tissue-preferred promoters can be utilized to target enhanced CLV3-like sequence expression within a particular plant tissue. Tissue-preferred promoters include, for example, shoot meristem-preferred promoters as described in Atanassova et al. (1992) *Plant J.* 2:291, U.S. Pat. No. 6,239,329; which is herein incorporated by reference. In addition, the promoter of the KNOTTED1 gene can be used to direct shoot meristem-preferred expression (Dorien et al. (2002) *Plant Molecule Biology* 48:423–441 and Tomoaki et al. (2001) *Genes and Development* 15:581–590, both of which are herein incorporated by reference). Alternatively, the promoter of the REVOLUTA gene could be used for meristem-preferred expression. See, for example, Genbank Accession No. AC024594 (Rice) and AB005246 (*Arabidopsis*), both of which are herein incorporated by reference. One of skill in the art will recognize the promoter can encompass up to 0.5 Kb, 1 Kb, 2 Kb, or more of the sequences flanking the coding region of these genes. Such promoters can be modified, if necessary, for weak expression.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the a CLV3-like sequence of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191; 5,889,190; 5,866,785; 5,589,367 and 5,316,931; herein incorporated by reference.

The method of transformation/transfection is not critical to the instant invention; various methods of transformation or transfection are currently available. Thus, any method, which provides for effective transformation/transfection may be employed. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro CellDev. Biol.* 27P:175–182 (soybean); Singh et al., (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et a. (1995) "Direct DNA Transfer into Intact Plant Cells via Micro-projectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al., (1983) *Gene* 22:229–235); Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous nucleotide sequences in yeast is well known (Sherman et al. (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353–365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al.(1983) *J. Virol.* 45:773–781). Additionally, gene sequences to control replication in the host cell may be incorporated into the vector such as those found in bovine papilloma virus type-vectors (Saveria-Campo (1985) *DNA Cloning Vol. II a Practical Approach*, D. M. Glover, Ed., IRL Press, Arlington, Va., pp. 213–238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler (1997) *Biochemical Methods in Cell Culture and Virology*, Dowden, Hutchinson and Ross, Inc.).

It is recognized that with these nucleotide sequences, antisense constructions, complementary to at least a portion of the messenger RNA (mRNA) for the CLV3-like sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774–8778; herein incorporated by reference.

Methods of Use

The present invention provides methods and compositions for modulating the level and/or activity of the CLV3-like polypeptides in a host cell, particularly, a plant or plant cell. In some embodiments, the level and/or activity of the CLV3-like polypeptide of the present invention is modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., U.S. Pat. No. 5,565,350 and PCT/US93/03868. In other embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the level and/or activity of polypeptides of the present invention in the plant. Plant forming conditions are well known in the art and discussed briefly, supra. Alternatively, the level and/or activity of the polypeptide of the invention may be modulated in a plant or plant cell by contacting the plant or plant cell with the polypeptide of the invention in the form of a chemical spray.

In general, the activity and/or level of the CLV-3 like polypeptide is modulated (increased or decreased) by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly maize.

The present invention further provides compositions and methods for modulating plant development and/or developmental pathways. Accordingly, the CLV3-like sequences of the invention find use in controlling or modulating cell division, differentiation, and development. In particular, the sequences of the present invention find use in modulating meristem development.

By "modulating meristem development" is intended any alteration in the meristem phenotype including, for example, an alteration in the formation and maintenance of the meristem and/or an alteration of size and appearance of shoot and floral meristems. Such modulations in meristem development may result in an increased or a decreased yield of leaves, flowers, and/or fruit.

The disruption of the CLAVATA pathway in the maize fea2 mutants produced up to twice the normal number of rows of seeds in the maize ear (Taguchi-Shiobara et al. (2001) *Genes and Development* 15:2755–2766). As row number or spikelet density variants are of importance in other cereals such as barley, wheat, and rice, modulating the CLV pathway may find use in improving crop yields. Accordingly, methods of the present invention find use in modulating the level of the CLV3 polypeptide in a plant. As the CLV3-like sequences of the present invention are predicted to limit the growth of meristem structures by regulating cell division in the meristem. Accordingly, specific embodiments of the present invention comprise the expression of the CLV3-like sequences such that a decreased level and/or activity of the endogenous CLV3-like sequences occurs. The decrease in CLV3-like activity or level can cause loss of normal control of cell division in shoot apical meristems and in floral meristems. In either case, the loss of cell division will present as an enlargement of the meristem. In shoot apical meristems this enlargement can lead to fasciation, where the meristem grows large, causing the stem to become straplike, and leaves and flowers to be produced in great profusion. In flowers, the enlargement leads to an increase in the number of floral organs, including an increase in carpel number, which increases fruit size and seed numbers.

Hence, expression of the CLV3-like sequences of the invention in a manner that results in a decreased activity or level of the CLV3-like polypeptide can result in: 1) the generation of additional leaves before flowering begins, thereby providing plants having greater energy production and thus increasing yield; 2) an increase in the number of seed-bearing carpels, thereby allowing for the production of additional seeds; 3) the generation of a thicker stem thereby preventing crop lodging, increasing wind resistance ect.; 4) an alteration of the fruit of the plants (i.e., an increase in size, shape, and/or the number of fruit per plant); and, 5) an increase in the number of flowers. Plants exhibiting modulated meristem development as described above can be selected using visual observation. See, for example, U.S. Pat. Nos. 5,637,785; 6,002,069; 5,859,338; 6,025,483, and Fletcher et al. (1999) *Science* 283:1911–1914, all of which are herein incorporated by reference.

As discussed in more detail above, methods are known in the art that will result in a decreased level and/or activity of the CLV3-like polypeptide. For example, an antisense construct of a CLV3-like sequences can be expressed in a plant or plant cell to reduce the level or activity of the endogenous CLV3-like sequence. In this embodiment, the level of a polypeptide in a host cell is modulated and comprises providing a plant cell comprising an mRNA having the sequence set forth in SEQ ID NO:1, 3, 4 or a variant or fragment thereof; and, introducing a nucleotide sequence comprising at least 15 consecutive nucleotides of SEQ ID NO:1, 3, or 4 into the plant or plant cell, wherein the expression of the nucleotide sequence inhibits expression of the mRNA in the plant or plant cell.

Alternatively, transformation with a CLV3-like sequence can result in cosuppression of the endogenous CLV3-like sequence. In addition, modifications can be made to the CLV3-like sequences of the invention that result in the CLV3-like sequence having a dominant negative activity. In each of the instances described above, transformation of a plant or plant cell with the appropriate CLV3-like sequences will result in a decrease level or activity of the endogenous CLV3-like sequences, resulting in meristem enlargement. Alternatively, the polypeptide having dominant negative activity can be contacted with the plant or plant cell in the form of a chemical spray.

In one embodiment, the level or activity of the CLV3-like sequences are down regulated in maize. As the sequences of the invention are predicted to negatively regulate meristem maintenance genes, such as a maize homolog for WUSCHEL or POLTERGEIST, the method is therefore expected to regulate production capacity. This in turn will affect yields. In maize, an increased production capacity could be reflected by an increase in the size and shape of the ear and thereby affect kernel-production capacity of the ear. For a review, see, Fletcher et al. (2002) *Annul Review of Plant Biology* 53:45–66, herein incorporated by reference.

In another embodiment of the invention, methods are provided to increase the level and/or activity of the endogenous CLV3-like sequence in a plant or plant cell. The increase in CLV3-like activity or level is predicted to cause a decrease in meristem growth. Such an alteration in growth may present as a shorter ear and as a decrease in spikelet formation. Such a phenotype finds use in producing plants having a higher kernel carrying potential and an enhanced yield stability under a variety of stress-prone conditions (i.e., drought, high density plantings, etc.).

For instance, over expression of the CLV3-like sequences of the invention may find use in increasing grain yields under drought conditions. Many factors have been identified that contribute to higher plant performance under water deficiencies. Improved maize yield performance under drought stress was accompanied by shorter ears (possibly due to better silking synchronizations resulting in efficient pollinations or quicker escape from the stress by shortened ear development duration). In addition, phenotypic changes in drought-tolerant maize plants include increased kernel carrying capacity due to reduced barrenness under drought conditions. In fact, drought tolerant maize have a reduction in the number of spikelets formed on the ear and thus overall seed set is facilitated by reducing water and carbon requirements per spikelet. Thus, while fewer spikelets are formed on the ear, each spikelet is ultimately more successful in forming grain, especially under drought conditions. See, for a review, Bruce et al. (2002) *Journal of Experimental Botany* 53:1–13, which is herein incorporated by reference. Hence, increasing the level and/or activity of the CLV3-like sequences of the invention in a plant or plant cell may find use in producing plants having a higher kernel carrying capacity on a per square foot of land and further enhance yield stability in a variety of stress-prone conditions (i.e., drought or high density plantings).

Any means known in the art can be used to increase the level and/or activity of the CLV3-like sequences in a plant. In one embodiment, the polypeptide is contacted with the plant in the form of a chemical spray at time of drought. In yet another embodiment, the CLV3-like sequence is expressed in the plant. In this embodiment, the CLV3-like sequence may be operably linked to a drought-inducible promoter. Such promoters are known in the art and have been described elsewhere herein.

As discussed above, the CLV3-like polypeptides and variants and fragments thereof of the present invention can be presented to the plant or plant cell as a chemical spray. In this embodiment, the CLV3-like polypeptide or variants or fragments thereof, are presented to the plant or plant cell during an appropriate stage of development or under the appropriate environmental conditions in amounts sufficient for the polypeptide to modulate meristem development. The compositions can be applied to the plant or plant cell by, for example, spraying, atomizing, dusting, scattering, coating or pouring. It is recognized that any means to bring the CLV3-like polypeptides in contact with the plant can be used in the practice of the invention.

The polypeptides of the invention can be formulated with an acceptable carrier into a composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances. Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids, and fertilizers, can be combined with carriers, surfactants, or adjuvants customarily employed in the art of formulation or other components to facilitate product handling and application for particular target mycotoxins. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as concentrate of primary composition, which requires dilution with a suitable quantity of water or other diluent before application. The concentration will vary depending upon the nature of the particular formulation, specifically, whether it is a concentrate or to be used directly.

In a further embodiment, the compositions, as well as the polypeptides of the present invention can be treated prior to formulation to prolong the activity when applied to the plant or plant cell as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W. H. Freeman and Co.).

The present invention further provides a method of genotyping a plant using the polynucleotide of the present invention. As discussed above, the CLV3-like sequences of the invention regulate meristem development. The sequences therefore find use as molecular markers for the selection of plants that will have the desired developmental phenotype. For instance, specific alleles of the CLV3-like sequences of the invention could be used to trace maize hybrids that form long or short ears.

Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, Paterson (1996) *The DNA Revolution* (Chapter 2) in: *Genome Mapping in Plants* (ed. Andrew H. Paterson), Academic Press/R. G. Lands Company, Austin, Tex., 7–21.

The particular method of genotyping in the present invention may employ any number of molecular marker analytic techniques such as, but not limited to, restriction fragment length polymorphism's (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention, in preferred embodiments, the probes are selected from polynucleotides of the present invention. Typically, these probes are cDNA probes or restriction enzyme treated (e.g., PST I) genomic clones. The length of the probes is discussed in greater detail, supra, but is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in haploid chromosome compliment. Some exemplary restriction enzymes employed in RFLP mapping are EcoRl, EcoRv, and Sstl. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample, preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

EXPERIMENTAL

Example 1

Isolation of CLV3-like Sequences and Expression Patterns in Maize

CLAVATA3 is a short secreted protein that acts as a "ligand" and interacts with a receptor kinase complex (CLAVATA1 & CLAVATA2) and thereby regulates the pool of stem cells in the plant shoot meristem. The signaling complex negatively regulates homeodomain genes that are necessary to maintain a meristem structure. In *Arabidopsis* WUSCHEL is regulated by the CLV pathway. The original CLV3 gene was described in *Arabidopsis* but no other functional homolog have been described in other plant species.

Using an extended version of the conserved region from AtCLV3 (LHEELRTVPSGPDPLHHHVNPPRQR) (SEQ ID NO:6) the sequence set forth in SEQ ID NO:1 was identified in a maize library (5 days after silking ovules) that may have included meristematic tissues. The predicted protein is approximately the same length as AtCLV3 and it contains the conserved amino acid sequence as set forth in FIGS. 1 and 3.

A genomic clone of the maize CLV3-like sequence of the invention was also isolated. Specifically, mutator insertion point primers from a proprietary maize library were used to generate from PCR cloning the maize genomic fragment set forth in SEQ ID NO:4. The start and stop codons are highlighted by bold in FIG. 4. This genomic fragment contains two introns (similarly placed to the *Arabidopsis* CLV3 gene) that are indicated by lower-case, italics sequences in FIG. 4.

It is noted that the nucleotide sequence of SEQ ID NO:4 (the CLV3-like sequence derived from the genomic clone) and the sequence set forth in SEQ ID NO:1 and 3 differ slightly. The differences are possibly due to differences in genotypes used in the making the EST libraries. Therefore the "polymorphisms" between SEQ ID NO:1, SEQ ID NO:3 and SEQ ID NO:4 may be real.

A CLV3 homolog is predicted to be more active in the immature ear tissue of a short ear line than in a long ear line, since this gene would negatively regulate meristem maintenance genes such as a maize homolog of WUSCHEL or POLTERGEIST. A Lynx MPSS experiment was performed on samples from two elite inbreds with contrasting early ear development. Expression levels of maize orthologs of CLV3 and CLV2 in whole immature ears from long ear (LE) and short ear (SE) inbred lines at two vegetative stages, V11 and V12, were analyzed. Total RNA was prepared from pools of dissected immature ears from approximately 40 plants grown in the field per developmental stage and genotype. The RNA was used in an MPSS analysis by Lynx Therapeutics (Haywood, Calif.) and data are reported as parts per million (ppm) essentially as described in Brenner et al. (2000) *Nature Biotechnology* 18:630:634. See FIG. 2. CLV2 refers to the maize FEA2 gene (Taguchi-Shiobara et al.

(2001) *Genes & Rev* 15:2755–66) and CLV3 refers to the maize CLV3 clone of the present invention.

As predicted for a CLV3 homolog, the expression of the maize CLV3-like sequence (SEQ ID NO:1) was shown in the Lynx MPSS data to be more active in a short ear elite maize line (A) than in a long ear line (D). See FIG. 2. This data supports that the CLV3-like sequence of the present invention is a maize homolog to the *Arabidopsis* CLV3 gene. Hence, by negatively regulating meristem maintenance genes, CLV3 may play a strong role in regulating the size and shape of the maize ear thus affecting kernel-production capacity of the ear. This in turn would play a role in affecting yields. It is further noted that CLV3 is weakly expressed just in the meristematic regions throughout the ear and therefore the functional signal was dependent on CLV3 whose expression is more highly restricted and rate limiting than expression of FEA2.

Example 2

Transformation and Regeneration of Transgenic Plants

Immature maize embryos from greenhouse donor plants are bombarded with a plasmid containing the CLV3-like sequence operably linked to the drought-inducible promoter RAB17 promoter (Vilardell et al. (1990) *Plant Mol Biol* 14:423–432) and the selectable marker gene PAT, which confers resistance to the herbicide Bialaphos. Alternatively, the selectable marker gene is provided on a separate plasmid. Transformation is performed as follows. Media recipes follow below.

Preparation of Target Tissue:

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA:

A plasmid vector comprising the CLV3-like sequence operably linked to an ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water

10 μl (1 μg) DNA in Tris EDTA buffer (1 μg total DNA)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment:

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment:

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel-earring capacity yields under drought conditions when compared to control maize plants under identical environmental conditions. Alternatively, the transformed plants can be monitored for a modulation in meristem development (i.e., a decrease in spikelet formation on the ear). See, for example, Bruce et al. (2002) *Journal of Experimental Botany* 53:1–13.

Bombardment and Culture Media:

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-1$H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I H$_2$O), sterilized and cooled to 60° C.

Example 3

*Agrobacterium*-mediated Transformation

For *Agrobacterium*-mediated transformation of maize with an antisense sequence of the CLV3-like sequence of the present invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the antisense CLV3-like sequences to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Plants are monitored and scored for a modulation in meristem development. For instance, alterations of size and appearance of the shoot and floral meristems and/or increased yields of leaves, flowers, and/or fruits.

Example 4

Soybean Embryo Transformation

Soybean embryos are bombarded with a plasmid containing an antisense CLV3-like sequences operably linked to an ubiquitin promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising an antisense CLV3-like sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Sunflower Meristem Tissue Transformation

Sunflower meristem tissues are transformed with an expression cassette containing an antisense CLV3-like sequences operably linked to a ubiquitin promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant,* 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) *Plant Mol. Biol.* 18:301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the CLV3-like gene operably linked to the ubiquitin promoter is introduced into *Agrobacterium* strain EHA105 via freeze-thawing as described by Holsters et al. (1978) *Mol. Gen. Genet* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by CLV3-like activity analysis of leaf extracts while transgenic seeds harvested from NPTII-positive $T_0$ plants are identified by CLV3-like activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive (i.e., a decrease in CLV3-like expression) explants are identified, those shoots that fail to exhibit a decrease in CLV3-like activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for a decreased CLV3-like expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 6

Quantitiative Reverse Transcription-PCR Analysis of CLV3-like Gene in Maize Developing Ears Example 1 described the Lynx MPSS expression differences for the CLV3-like gene in the ear RNA samples of two elite inbred lines, A and D producing short and long ears, respectively. Ear tip RNA samples from three developmental stages were queried by quantitative RT-PCR essentially as described. Immature ear tips (0.5–1 mm) from A and D were harvested at the V11 and V12 stages of development. Total RNA was isolated from the immature ear-tip tissues using Trizol reagent (Invitrogen, Carlsbad, Calif., USA) with the Phase Lock Gel System (Eppendorf, Westbury, N.Y., USA). Twenty micrograms of total RNA were pretreated with Rnase-free DNase I (Ambion, Austin, Tex., USA) of which 3 µg were used for first-strand cDNA synthesis (Superscript II Kit, Invitrogen, Carlsbad, Calif., USA). Multiplex PCR was performed using 1 µL of first-strand cDNA as template in a 25 µL reverse transcriptase reaction along with HotStar Taq DNA polymerase (Qiagen, Valencia, Calif., USA) according to the recommendations of the manufacturer. Thirty cycles were used for the simultaneous amplification of a CLV3-like gene (0.5 µM, 62559 Zmclv3-F, 5'-TCT-TCGTCGACCTTGAACCCACTGT-3') (SEQ ID NO:9) and (0.5 µM 62561 Zmclv3-R, 5'-AAGACCACAAACTTC-CAGGMGCGAGG-3') (SEQ ID NO:10) and tubulin (0.1 µM 62961 Zmtub-F, 5'-TCTTCGTCGACCTTGAAC-CCACTGT-3') (SEQ ID NO:11) and 0.1 µM 47209 Zmtub-R, 5'-MCACCAAGAATCCCTGCAG CCCAGTGC-3') (SEQ ID NO:12) cDNA. PCR was performed using a three step protocol that was preceded by an initial incubation at 95° C. for 15 minutes: denaturation, 94° C. for 45 sec.; annealing, 60° C. for 45 sec.; extension, 72° C. for 1.5 min. In a separate experiment, the number of PCR cycles and primer and template concentrations were shown to be in the linear range of amplification for both genes from the PCR reaction. Amplicons were separated on a 1.5% ethidium bromide-stained agarose gel. Agarose gels were analyzed on a short wave (310 nm) UV transilluminator and captured using CCD imaging with the Quantity One image analysis/quantitation software from Bio-Rad (Hercules, Calif., USA). This same software was used for the florescence quantification and normalization of the amplified DNA fragments.

The relative expression level of the CLV3-like gene from maize inbred A was nearly 2-fold greater (P<0.007) than the expression level from inbred D for the two early stages of ear development. The differential expression of the CLV3-like gene between the two inbreds was less pronounced once the ears have fully terminated the development of new florets, essentially when the inflorescence meristem ceases. These data show a indirect correlation with CLV3-like mRNA abundance and duration of IM activity. The lower the CLV3-like expression, the longer the IM activity exists during ear development resulting in more spikelets per row and potentially greater yields.

Example 7

*Arabidopsis* Transformed with 35S::maize CLV3-like Gene

The CLV3-like gene and a control gene, embryo surround region 1 (ESR1; Opsahl-Ferstad, et al. (1997) *Plant J.* 12:235–46) were cloned into a CaMV 35S promoter-containing vector such that the gene products are produced at constitutive levels in the transgenic *Arabidopsis* plants. These two constructs were transformed into *Arabidopsis* lines, Columbia (Col, wild-type) and Col clv1-4 and clv3-1 mutant lines by the following method: The CLV3-like and ESR1 genes full-length coding sequences were amplified using the corresponding cDNA clones as templates and following sets of primers. 1) Primer pairs for CLV3-like amplification: (zmCLV3-1, 5'-AAGGTCTCCTCGAGATG-GCTCACGCGGCCGTCGTC-3') (SEQ ID NO: 13) and (zmCLV3-2, 5'AAGGTCTCCTCGAGATCAAGGCGACT-GCCGCCTTG-3') (SEQ ID NO: 14); 2) Primer pairs for ESR1 amplification: (ESR1-1, 5'-AACTCGAGATTC-CATGGCATCAAGG-3') (SEQ ID NO: 15) and (ESR1-2, 5'-AATCTCGAGCTAGTATCTATCCGATAATG-3') (SEQ ID NO: 16). Amplified DNA fragments were cloned into pGEM-T Easy (Promega). Individual clones were isolated and sequenced to confirm that the cloned DNA contained no nucleotide sequence changes in ORFs. The correct DNA fragments were isolated from the vector using restriction enzymes, BsaI and XhoI, for CLV3-like and ESR1, respectively. These fragments were ligated into the XhoI-digested binary vector pBE851, which resulted in the fusion of each ORF with CaMV 35S promoter and 3' Nos terminator. The binary vector carried the bar gene as a selective marker in plants and KanR as a selective marker in bacteria. The binary constructs with corresponding genes were transformed into *Agrobacterium tumefaciens* and subsequently into three different *Arabidopsis* backgrounds, wild-type Columbia, clv1-4 and clv3-1 mutants using the in planta transformation method described by Bechtold, N. and G. Pelletier (1998). "In planta *Agrobacterium*-mediated transformation of adult *Arabidopsis thaliana* plants by vacuum infiltration." *Methods Mol Biol* 82: 259–66. The seed produced by the transformed plants was used to select T1 transgenic plants by applying BASTA herbicide several times at the seedling stage. More than 20 T1 plants for each construct and background were analyzed for their phenotypes.

It was previously shown that CaMV 35S-driven *Arabidopsis* CLV3 transformed into *Arabidopsis* produced diminutive plants where the shoot apical meristem is consumed early in the plant's development (Brand et al. (2000) *Science* 289:617–619). A similar phenotype was noted when the CaMV 35S-driven maize CLV3-like gene was transformed into *Arabidopsis* Col line. A few leaves were produced but no floral structure developed. Additionally, when the CLV3-like was transformed into the clv1-4 *Arabidopsis* mutant line, the plants were able to support floral development and morphology similar to the clv1-4 mutant line alone. These data suggest that the constitutively expressed CLV3-like gene functions the same as the constitutively expressed *Arabidopsis* CLV3 gene in transgenic plants and that it functions in the same pathway as CLV1 as predicted.

Figure 7:
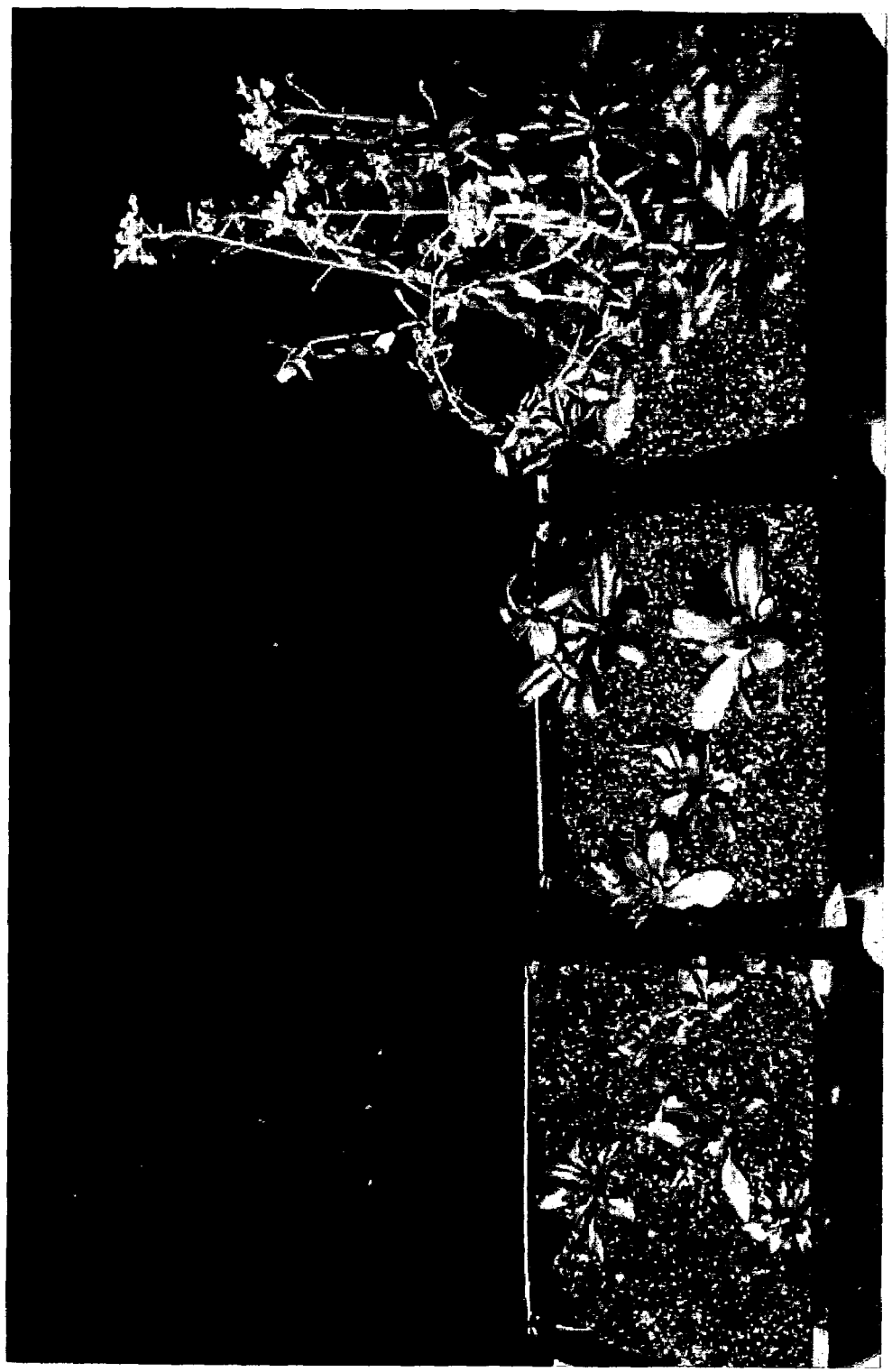
FIG. 7 is a photographic representation of the CLV1 activity requirement for expression of wuschel phenotype (caused by zmCLV3 constitutive expression). The plant box on the left is 35S::zmCLV3 in wild type tissue, the center plant box is 35S::zmCLV3 in clv3-1 plant tissue, and the plant box to the right is 35S::zmCLV3 in clv1-4.

FIGS. 5, 6 and 7 are photographic representations of the described expression patterns noted throughout the *Arabidopsis* transformation. The 35S::zmCLV3 is not expected to complement the clv3-1 mutation due to the fact that the 35S promoter produces far more product thus overwhelming the CLAVATA receptor and generating a phenotype similar to the 35S::zmCLV3-transformed wild types. The atCLV3 regulatory sequences were necessary to express the atCLV3 gene properly in transgenic *Arabidopsis* to restore the mutant back to normal (Brand et al. (2000) Science 289: 617–619). The lack of stunted phenotype in 35S::zmCLV3 expressed in clv1-4 mutant *Arabidopsis* line clearly demonstrates that the zmCLV3 functions in the CLAVATA pathway, requiring functional CLV1 protein to impart its overexpressed-derived stunted phenotype. In other words, the 35S::zmCLV3 product is affecting the transgenic *Arabidopsis* sp. in a similar manner as the 35S::atCLV3 product (Brand et al. (2000) Science 289:617–619) demonstrating that zmCLV3 is a functional ortholog of atCLV3. In all cases, the 35S::zmESR1 in *Arabidopsis*, acting as a control, did not confer any mutant or altered phenotypes as expected suggesting that only certain maize CLE can act as a counterpart for the atCLV3 function.

Example 8

Rice CLV3 Sequence

The maize CLV3-like gene was mapped to a region in Bin 4 of Chromosome 2 by linking a segregating polymorphism between the B73 and Mo17 CLV3-like alleles in the IBM population described by Sharopova, et al. (*Plant Mol Biol,* 2002. 48:463–81) to four different markers all mapping to this locus. This region in maize is syntenic to a region on chromosome 4 in rice. A single BAC clone from rice, OSJNBb0022F23, mapping to chromosome 4 contains an ORF homologous to the maize CLV3-like gene at coordinates 14468 to 14897 nt. Based on Fgenesh gene prediction program (from Softberry, Inc., Mount Kisco, N.Y. 10549), two introns were located within the predicted coding sequence from rice and in nearly the same sites as that of the maize CLV3-like and *Arabidopsis* CLV3 genes.

```
SEQ ID NO: 7 is a OsCLV3-Iike genomic nucleic acid sequence from rice-
(GCTCATCCTCAITGTGCCGICAAGCCGTGCTGCTGCTTCTGCTGCTGCTGCCT                                    (SEQ ID NO:7)

CCTCGTCGCCGCCGTGGTCGCCGTCGCCGTCTTTCTGGCCATGTCGCCGCCCG

CCGCCGCCGCCGCCGCCGCATCGTCGTCACAACCAGgtaggttcaaaaagtgcggggtctt ttcttgtaacgtgagttcttgacgacgcggcttttttgtagCGGCGGCGGCGGCATTGCAACGGGCCGA

GACGACGGCGACCATGTACACCGCGAAGGAGTTGCGGGAGAAGCAGGACGTG

ACCAAGgtcggtctgagctcaaaaaaaggtggctcttttcatggctttcttgccctgttcgatcgatctcatggtggtgta gggtttcttgatttggggggttgcagGGCGCGGAGGAGGACGTGACCACGACGACGACGACG

ACGGGGTTCGGCGCGGAGTCGGAGAGGGAGGTGCCCACCGGGCCGGACCCG

ATCCACCAGCACGGCCGGGGCCCAGGCGGCAGTCACCGTGAGTGCGAATCC

CCCGTCGGCGTCGCCGGGTTAACGAATCGGGCGTGAACCCAGAAICCCATGAG

ACGCGATGGTCTATGAAAGAAAGATTGTGCTCTICAATTCGTTTTGCTGAATCTG

TGATGCACTTGGGGATTTTATTCAGATTCATTTCTTGCTGTAGGGAACACAGTAG

TATGTCTGAA)

(note: start and stop in bold; introns are indicated by the underlined and
lowercase letters).
```

Sequence ID NO 8 is the OsCLV3 predicted protein encoded by the nucleic acid sequence of Seq ID NO:7. FIG. 8 contains the CLUSTALW-derived protein sequence alignment of rice and maize CLV3-like with the *Arabidopsis* CLV3 protein sequence using default settings.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

The present invention was described more fully above with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An isolated nucleic acid molecule selected from the group consisting of:
   (a) a nucleic acid molecule comprising a nucleotide sequence set forth in SEQ ID NO:1, 3, or 4;
   (b) a nucleic acid molecule comprising a nucleotide sequence encoding an amino acid sequence set forth in SEQ ID NO:2; and
   (c) a nucleic acid molecule comprising a nucleotide sequence having at least 90% sequence identity to the sequence set forth in SEQ ID NO:1, 3 or 4, wherein said sequence encodes a polypeptide that limits meristem growth when expressed.

2. An expression cassette comprising the nucleic acid of claim 1 operably linked to a regulatory element that drives expression.

3. An expression vector comprising the expression cassette of claim 2.

4. A host cell comprising the expression vector of claim 3.

5. The cell of claim 4, wherein said cell is a plant cell.

6. The cell of claim 4, wherein said cell is a bacterial cell.

7. A plant having stably incorporated into its genome at least one nucleotide construct comprising a nucleotide sequence operably linked to a heterologous promoter that drives expression in said plant, wherein said nucleotide sequence is selected from the group consisting of:
   (a) a nucleic acid molecule comprising a nucleotide sequence set forth in SEQ ID NO:1, 3, or4;
   (b) a nucleic acid molecule comprising a nucleotide sequence encoding an amino acid sequence set forth in SEQ ID NO:2; and
   (c) a nucleic acid molecule comprising a nucleotide sequence having at least 90% sequence identity to the sequence set forth in SEQ ID NO:1, 3 or 4, wherein said sequence encodes a polypeptide that limits meristem growth when expressed.

8. The plant of claim 7, wherein said promoter is a constitutive promoter.

9. The plant of claim 7, wherein said promoter is a tissue-preferred promoter.

10. The plant of claim 7, wherein said promoter is an inducible promoter.

11. The plant of claim 7, wherein said plant is a monocot.

12. The plant of claim 11, wherein said monocot is maize, wheat, rice, barley, sorghum, or rye.

13. The plant of claim 7, wherein said plant is a dicot.

14. The transformed seed of the plant of claim 7.

* * * * *

SEQUENCE LISTING

```
<160> NUMBER OF SEQ ID NOS: 16

<210> SEQ ID NO 1
<211> LENGTH: 740
<212> TYPE: DNA
<213> ORGANISM: Zea mays

<400> SEQUENCE: 1
gcagagggtt ttggagcagg caagcctggc tcttcttgtt cctccatctc ttccgtcgcc      60
ttgcgcgtgt tggcggctgc gtacgcgagg ccgccgcgtc tggccggatg gctcacgcgg     120
ccgtcgtcgc cttgctcgcc gtcgctgtga tcttggcctg cttgccgccg cccgccgcct     180
cgtcctaccg gggagcggct gcattgcgac ggctcgagac agcggagccc atggacaccg     240
cgcagggctt gcgggagaag gcggacgtga acaagggcgc ggaggaggac ctgagcacga     300
cagggttcgg cgccgagtcg gagagggagg tgccgacggg accggacccc atccaccacc     360
acgcccgggg gccaaggcgg cagtcgcctt gatcgtcatg cgcgcgcgac acggcggcgg     420
tggatcctcg cttcctggaa gtttgtggtc ttgatcaggc gggcgtgaac cggattccac     480
gatgatcctg ctctttcttt gttcttaaat gtatctgcca tgcacctttg gttctaattc     540
cattgttgta gtagggaagc agcatccacc tatcaactat catcaaaacc ccctatgtt     600 ttggcgtgcc aattagagaa agggaattac agcgcgattc atataataag tgtgtacaat     660
gaattccacg tatgagttgt tctttccctc gtaattttgt catcttgttt tgttgctggt     720
tcaaaaaaaa aaaaaaaaaa                                                 740

<210> SEQ ID NO 2
<211> LENGTH: 94
<212> TYPE: PRT
<213> ORGANISM: Zea mays

<400> SEQUENCE: 2

Met Ala His Ala Ala Val Val Ala Leu Leu Ala Val Ala Val Ile Leu
 1               5                  10                  15

Ala Cys Leu Pro Pro Pro Ala Ala Ser Ser Tyr Arg Gly Ala Ala Ala
                20                  25                  30

Leu Arg Arg Leu Glu Thr Ala Glu Pro Met Asp Thr Ala Gln Gly Leu
            35                  40                  45

Arg Glu Lys Ala Asp Val Asn Lys Gly Ala Glu Glu Asp Leu Ser Thr
        50                  55                  60

Thr Gly Phe Gly Ala Glu Ser Glu Arg Glu Val Pro Thr Gly Pro Asp
65                  70                  75                  80

Pro Ile His His His Ala Arg Gly Pro Arg Arg Gln Ser Pro
                85                  90

<210> SEQ ID NO 3
<211> LENGTH: 282
<212> TYPE: DNA
<213> ORGANISM: Zea mays

<400> SEQUENCE: 3
atggctcacg cggccgtcgt cgccttgctc gccgtcgctg tgatcttggc ctgcttgccg      60
```

```
ccgcccgccg cctcgtccta ccggggagcg gctgcattgc gacggctcga gacagcggag      120
cccatggaca ccgcgcaggg cttgcggag aaggcggacg tgaacaaggg cgcggaggag       180
gacctgagca cgacagggtt cggcgccgag tcggagaggg aggtgccgac gggaccggac      240
cccatccacc accacgcccg ggggccaagg cggcagtcgc ct                         282

<210> SEQ ID NO 4
<211> LENGTH: 826
<212> TYPE: DNA
<213> ORGANISM: Zea mays

<400> SEQUENCE: 4
accagacggg cgaaaccaac tctctgcggc agagggcgga cggcagaggg tcttggagca       60
ggcaagcctg gctcttcttg ttcctccatc tcttccgtcg ccttgcgcgt gttggcgget     120 gcgtacgcga ggccgccgcg tctggccgga tggctcacgc ggccgtcgtc gccttgctcg     180
ccgtcgctgt gatcttggcc tgcttgccgc cgcccgccgc ctcgtcctac cggggaggta     240
cgtaaaacgc gcgcccgcgc gcatcgcaaa ccaaaccgtg ttttcttggt tcttccgggc     300
gcacccaaaa cctgacgttt tcgcccgcgg cacagcggct gcattgcgac ggctcgagac     360
agcggagccc atggacaccg cgcagggctt gcgggagaag gcggacgtga acaaggtaaa     420
aatacaaaga cgcccgccgc cgtgctgcgg gctagggtca aggaaaggcg gctctttttt     480
ctgctggtct ttttcgattc tccggctcga tcttccggcg tgcagggcgc ggaggaggac     540
ctgagcacga cagggttcgg cgccgagtcg gagagggagg tgccgacggg accggacccc     600
atccaccacc acgcccgggg gccaaggcgg cagtcgcctt gatcgtcatg cgcgcgcgac     660
acggcggcgg tggatcctcg cttcctggaa gtttgtggtc ttgatcaggc gggcgtgaac     720
cggattccac gatgatcctg aagggcgaat tctcttaaat gtatctgcca tgcacctttg     780
gttctaattc cattgttgta gtagggaagc agcatccacc tatcaa                     826

<210> SEQ ID NO 5
<211> LENGTH: 36
<212> TYPE: PRT
<213> ORGANISM: Arabidopsis thaliana

<400> SEQUENCE: 5

Gly Glu Ala Glu Lys Ala Lys Thr Lys Gly Leu Gly Leu His Glu Glu
 1               5                  10                  15

Leu Arg Thr Val Pro Ser Gly Pro Asp Pro Leu His His Val Asn
            20                  25                  30

Pro Pro Arg Gln
        35

<210> SEQ ID NO 6
<211> LENGTH: 25
<212> TYPE: PRT
<213> ORGANISM: Arabidopsis thaliana

<400> SEQUENCE: 6

Leu His Glu Glu Leu Arg Thr Val Pro Ser Gly Pro Asp Pro Leu His
 1               5                  10                  15

His His Val Asn Pro Pro Arg Gln Arg
            20                  25

<210> SEQ ID NO 7
<211> LENGTH: 706
<212> TYPE: DNA
```

<213> ORGANISM: Rice

<400> SEQUENCE: 7

```
gctcatcctc attgtgccgt caagccgtgc tgctgcttct gctgctgctg cctcctcgtc    60
gccgccgtgc tcgccgtcgc cgtctttctg gccatgtcgc cgcccgccgc cgccgccgcc   120
gccgcatcgt cgtcacaacc aggtaggttc aaaaagtgcg gggtcttttc ttgtaacgtg   180
agttcttgac gacgcggctt tttgtagcgg cggcggcggc attgcaacgg gccgagacga   240
cggcgaccat gtacaccgcg aaggagttgc gggagaagca ggacgtgacc aaggtcggtc   300
tgagctcaaa aaaggtggc tcttttcatg gctttcttgc cctgttcgat cgatctcatg   360
gtggtgtagg gtttcttgat ttgggggtt gcagggcgcg gaggaggacg tgaccacgac   420
gacgacgacg acgggttcg cgcggagtc ggagagggag gtgcccaccg ggccggaccc   480
gatccaccac cacggccggg ggcccaggcg gcagtcaccg tgagtgcgaa tcccccgtcg   540
ccgtcgccgg gttaacgaat cggcgtgaa cccagaatcc catgagacgc gatggtctat   600
gaaagaaaga ttgtgctctt caattcgttt tgctgaatct gtgatgcact tggggatttt   660
attcagattc atttcttgct gtagggaaca cagtagtatg tctgaa              706
```

<210> SEQ ID NO 8
<211> LENGTH: 86
<212> TYPE: PRT
<213> ORGANISM: rice

<400> SEQUENCE: 8

```
Met Ser Pro Pro Ala Ala Ala Ala Ala Ala Ser Ser Ser Gln Pro
  1               5                  10                  15

Ala Ala Ala Ala Ala Leu Gln Arg Ala Glu Thr Thr Ala Thr Met Tyr
             20                  25                  30

Thr Ala Lys Glu Leu Arg Glu Lys Gln Asp Val Thr Lys Gly Ala Glu
         35                  40                  45

Glu Asp Val Thr Thr Thr Thr Thr Thr Gly Phe Gly Ala Glu Ser
     50                  55                  60

Glu Arg Glu Val Pro Thr Gly Pro Asp Pro Ile His His His Gly Arg
 65                  70                  75                  80

Gly Pro Arg Arg Gln Ser
                 85
```

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9

```
tcttcgtcga ccttgaaccc actgt                                        25
```

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10

```
aagaccacaa acttccagga agcgagg                                      27
```

```
<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
tcttcgtcga ccttgaaccc actgt                                          25

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
aacaccaaga atccctgcag cccagtgc                                       28

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
aaggtctcct cgagatggct cacgcggccg tcgtc                               35

<210> SEQ ID NO 14
<211> LENGTH: 35
<212> TYPE: DNA
<213> ORGANISM: Artificial Sequence
<220> FEATURE:
<223> OTHER INFORMATION: Primer

<400> SEQUENCE: 14
aaggtctcct cgagatcaag gcgactgccg ccttg                               35

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
aactcgagat tccatggcat caagg                                          25

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
aatctcgagc tagtatctat ccgataatg                                      29
```